US009662362B2

(12) United States Patent
Dockter

(10) Patent No.: US 9,662,362 B2
(45) Date of Patent: *May 30, 2017

(54) COMPOSITION AND METHODS FOR CLOTTING BLOOD

(71) Applicant: BYZMED LLC, Cottage Grove, WI (US)

(72) Inventor: Greg Dockter, Cottage Grove, WI (US)

(73) Assignee: ByzMed LLC, Cottage Grove, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 13/789,121

(22) Filed: Mar. 7, 2013

(65) Prior Publication Data

US 2013/0183393 A1 Jul. 18, 2013

Related U.S. Application Data

(62) Division of application No. 13/203,294, filed as application No. PCT/US2010/025413 on Feb. 25, 2010, now Pat. No. 8,414,935.

(60) Provisional application No. 61/155,423, filed on Feb. 25, 2009.

(51) Int. Cl.
| A61K 36/53 | (2006.01) |
| A61K 9/00 | (2006.01) |
| A61K 36/185 | (2006.01) |
| A61K 36/28 | (2006.01) |
| A61L 26/00 | (2006.01) |

(52) U.S. Cl.
CPC ............ *A61K 36/53* (2013.01); *A61K 9/0043* (2013.01); *A61K 36/185* (2013.01); *A61K 36/28* (2013.01); *A61L 26/0057* (2013.01); *A61L 26/0066* (2013.01); *A61L 2300/30* (2013.01); *A61L 2300/418* (2013.01); *A61L 2400/04* (2013.01)

(58) Field of Classification Search
None
See application file for complete search history.

(56) References Cited

U.S. PATENT DOCUMENTS

| 5,316,760 | A | * | 5/1994 | Voerman ..................... 424/58 |
| 5,854,291 | A | | 12/1998 | Laughlin et al. |
| 5,997,876 | A | | 12/1999 | Shikhashvili et al. |
| 2004/0076688 | A1 | | 4/2004 | Park |
| 2006/0198905 | A1 | | 9/2006 | Jain |
| 2008/0014251 | A1 | | 1/2008 | Benz et al. |
| 2008/0279902 | A1 | | 11/2008 | Luria |

FOREIGN PATENT DOCUMENTS

| CN | 1 141 180 | 1/1997 |
| KR | 2003-0004605 | 1/2003 |
| KR | 10-0628429 | 9/2006 |
| RU | 2000805 | 10/1993 |
| RU | 2109506 | 4/1998 |
| WO | WO 89/10737 | 11/1989 |
| WO | WO 2004/062370 | 7/2004 |
| WO | WO 2005/046632 | 5/2005 |

OTHER PUBLICATIONS

Archillea millefolium 2016 http://bioweb.uwlax.edu/bio203/2011/martinso_kris/interactions.htm.*
Urtica dioica 2016 http://thunderbaycountrymarket.com/resources/vendors/BFT_Nettle_info.pdf.*
Ishida et al., "Studies on the Antihemostatic Substances in Herbs Classified as Hemostatics in Traditional Chinese Medicine. I. On the Antihemostatic Principles in *Sophora japonica* L.," *Chem. Pharm. Bull.*, vol. 36, No. 6, pp. 1616-1618, 1989.
Li et al., "Experimental Study on the Hemostatic Activity of the Tibetan Medicinal Herb *Lamiophlomis rotata*," *Phytotherapy Research*, vol. 22, pp. 759-765, 2008.
Shaving with essential oils [retrieved on Oct. 8, 2013] retrieved from the Internet <URL: http://alexandrateagan.wordpress.com/2008/05/18/shaving-with-es sential-oils/> published May 18, 2008.
Ayurvedic Herb Uses [retrieved on Oct. 11, 2013] retrieved from the Internet <URL: http://web.archive.org/web/20080110204306/http://www.herbies-herbs.com/pages/AyurvedicHerbUses.htm> published on Jan. 10, 2008 as per Wayback Engine.
*Aconitum napellus* L. Aconit [retrieved on Oct. 11, 2013] retrieved from the Internet <URL: http //web.archive.org/web/20071122105934/http: //www.avogel.ch/en/plant-encyclopaedia/aconitum_napellus.php> published on Nov. 22, 2007 as per Wayback Engine.
First Examination Report issued Oct. 14, 2013, by the Australian Patent Office for corresponding Australian Patent Application No. 2010217955, filed Feb. 25, 2010, 8 pp.
Fedorova, Z.D., "Prevention of Hemorrhage in Dispensarized Patients With Congenital Thrombocytic Disorders," *Gematologiya I Transfuziologiya*, vol. 31, No. 11, pp. 25-28, 1987 (English abstract only).
Mackay, "Hemmorrhoids and Varicose Veins: A Review of Treatment Options," *Alternative Medicine Review*, vol. 6, No. 2, pp. 126-140, Jan. 1, 2001.
Second Examination Report issued Feb. 25, 2014, by the Australian Patent Office for corresponding Australian Patent Application No. 2010217955, filed Feb. 25, 2010, 11 pp.
Extended European Search Report issued Apr. 8, 2014, by the European Patent Office for corresponding EPC Patent Application No. 10746833.2, filed Feb. 25, 2010, 34 pp.

(Continued)

*Primary Examiner* — Terry A McKelvey
*Assistant Examiner* — Catheryne Chen
(74) *Attorney, Agent, or Firm* — Schwabe Williamson & Wyatt, P.C.

(57) ABSTRACT

Disclosed herein are compositions and methods for use of such for clotting blood. In one example, a disclosed composition includes at least *Stachys betonica*, *Achillea millefolium*, *Marrubium vulgare*, and *Urtica dioica*. Methods of use of the disclosed compositions are also provided, including methods of preventing or inhibiting a nosebleed, bleeding associated with a hemorrhoid or bleeding associated with a wound, such as a cut or abrasion.

9 Claims, No Drawings

(56) References Cited

OTHER PUBLICATIONS

Edemeka and Ogwu, Blood coagulation activities of the leaf extracts of *Ocimum gratissimum* plant in man, *J. Herbs Spices Medicinal Plants*, 7/4: Sep. 14, 2000.

Examination Report issued by the Canadian Intellectual Property Office on Dec. 2, 2015, for corresponding Canadian Patent Application No. 2,790,906.

El Bardai et al., "Comparative Study of the Antihypertensive Activity of *Marrubium vulgare* and of the Dihdropridine Calcium Antagonist Amiodipine in Spontaneously Hypertensive Rat," Clin Exp Hypertens, 26(6): 465-74, Sep. 2004. (downloaded from http://www.researchgate.net/publication/8173731_Comparative_study_of_the_antihypertensive_activity_of_Marrubium_vulgare_and_of_the_dihydropyridine_calcium_antagonist_amlodipine_in_spontaneously_hypertensive_rat.

El Bardai et al., "Pharmacological evidence of hypotensive activity of *Marrubium vulgare* and *Foeniculum vulgare* in spontaneously hypertensive rat," *Clin Exp Hypertens*, 23(4)329-43, May 2001. (downloaded from http://www.ncbi.nlm.nih.gov/pubmed/11349824).

Extended European Search Report issued by the European Patent Office, for corresponding European Patent Application No. 14191058.8, mailed Apr. 9, 2015, 11 pp.

Falk et al., "Isolation and identification of three new flavones from *Achillea millefolium* L.," *Journal of Pharmaceutical Sciences*, vol. 64, No. 11, pp. 1838-1842, Nov. 1, 1975.

Goker et al., "Haemostatic Actions of the Folkloric Medicinal Plan Extract Ankaferd Blood Stopper®," *Journal of International Medical Research*, vol. 36, No. 1, pp. 163-170, Jan. 1, 2008.

Kartsev et al., "Chemical Composition and Pharmacological Properties of Plants of the Genus *Stachys*," *Chemistry of Natural Compounds*, pp. 699-709, Nov. 1, 1994.

Sahpaz et al., "Isolation and pharmacological activity of phenylpropanoid esters from *Marrubium vulgar*," *Journal of Ethnopharmacology*, vol. 79, pp. 389-392, Mar. 30, 2002.

\* cited by examiner

COMPOSITION AND METHODS FOR CLOTTING BLOOD

CROSS REFERENCE TO RELATED APPLICATIONS

This application is a divisional of U.S. application Ser. No. 13/203,294, filed Aug. 25, 2011, which is the U.S. National Stage of PCT Application No. PCT/US2010/025413 filed Feb. 25, 2010 which claims the benefit under 35 U.S.C. 119(e) of the earlier filing date of U.S. Provisional Application No. 61/155,423, filed Feb. 25, 2009, all of which are incorporated herein by reference in their entirety.

FIELD

This disclosure relates to methods and compositions to stop bleeding, and specifically to a composition comprising a hemostatic active ingredient and an astringent ingredient for clotting blood.

BACKGROUND

Approximately 90 million people in the United States have a nosebleed in their lifetime and 400 million nosebleeds happen in the United States each year (in 45.5 million households). Approximately 2 million people use warfarin, a prescription blood thinner, which makes blood more difficult to clot. Approximately 3 million people have hemophilia and 60,000 people have HHT (a bleeding disorder) in the United States. Nosebleeds account for around 1 in 200 emergency room visits.

Currently, there is no well-delivered over-the-counter natural product to stop bleeding, such as nose bleeding.

SUMMARY

The present disclosure relates to compositions for clotting blood and uses thereof. The new compositions take advantage of the surprising finding that a hemostatic active ingredient and an astringent active ingredient obtained from natural sources, such as plants, effectively clot blood without causing discomfort to the subject. In one example, a blood clotting agent includes one or more hemostatic agents such as *Aconitum napellus, Agrimonia eupatoria, Aralia quinquefolia, Astragalus menziesii, Bellis perennis, Bixa orellana, Carduus benedictus, Equisetum arvense, Hamamelis virginiana, Helleborus niger, Hydrastis canadensis, Achillea millefolium, Salvia officinalis, Solidago virgaurea, Thlaspi bursa-pastoris, Urtica dioica, Vaccinium myrtillus, Viscum album, Zingiber officinale* and mixtures thereof and at least one astringent active ingredient, with astringent activity, such as *Acacia arabica, Agrimonia eupatoria, Azadirachta indica, Barosma, Bellis perennis, Bixa orellana, Carduus benedictus, Cimicifuga racemosa, Crataegus, Derris pinnata, Equisetum arvense, Euphrasia officinalis, Geranium maculatum, Geranium robertianum, Geum urbanum, Gnaphalium uliginosum, Hamamelis virginiana, Haronga madgascariensis, Hydrastis Canadensis, Hypericum perforatum, Iris versicolor, Juglans cinerea, Juniperus communis, Lamium album, Larix decidua, Lonicera caprifolium, Lycopus virginicus, Marrubium vulgare, Oxalis acetosella, Paullinia sorbilis, Plantago major, Ranunculus ficaria, Rhamnus frangula, Rheum, Schinus molle, Solidago virgaurea, Stachys betonica, Tribulus terrestris, Tussilago farfara, Urtica dioica, Vaccinium myrtillus* and mixtures thereof.

In one embodiment, a composition including at least *Stachys betonica, Achillea millefolium, Marrubium vulgare,* and *Urtica dioica.* is disclosed.

Also provided are pharmaceutical compositions including any of the disclosed compositions and an acceptable carrier/vehicle. In one example, the pharmaceutical composition is for use in the manufacture of a medicament or for use as a medicament.

Any of the disclosed compositions can be provided by methods known to those of ordinary skill in the art, including topical administration, such as by a cream, ointment, gel, lotion, patch, spray, solution, suspension, emulsion, powder, enema, suppository, or a combination thereof.

Methods of use of the disclosed compositions are also provided, including methods of preventing or inhibiting a nosebleed, bleeding associated with a hemorrhoid or bleeding associated with an open-wound, such as a cut or abrasion.

The foregoing and features of the disclosure will become more apparent from the following detailed description.

DETAILED DESCRIPTION OF SEVERAL EMBODIMENTS

I. Overview of Several Embodiments

Disclosed herein are compositions for clotting blood and uses thereof. In one example, a blood clotting agent includes one or more hemostatic agents such as *Aconitum napellus, Agrimonia eupatoria, Aralia quinquefolia, Astragalus menziesii, Bellis perennis, Bixa orellana, Carduus benedictus, Equisetum arvense, Hamamelis virginiana, Helleborus niger, Hydrastis canadensis, Achillea millefolium, Salvia officinalis, Solidago virgaurea, Thlaspi bursa-pastoris, Urtica dioica, Vaccinium myrtillus, Viscum album, Zingiber officinale* and mixtures thereof and at least one astringent active ingredient, with astringent activity, such as *Acacia arabica, Agrimonia eupatoria, Azadirachta indica, Barosma, Bellis perennis, Bixa orellana, Carduus benedictus, Cimicifuga racemosa, Crataegus, Derris pinnata, Equisetum arvense, Euphrasia officinalis, Geranium maculatum, Geranium robertianum, Geum urbanum, Gnaphalium uliginosum, Hamamelis virginiana, Haronga madgascariensis, Hydrastis Canadensis, Hypericum perforatum, Iris versicolor, Juglans cinerea, Juniperus communis, Lamium album, Larix decidua, Lonicera caprifolium, Lycopus virginicus, Marrubium vulgare, Oxalis acetosella, Paullinia sorbilis, Plantago major, Ranunculus ficaria, Rhamnus frangula, Rheum, Schinus molle, Solidago virgaurea, Stachys betonica, Tribulus terrestris, Tussilago farfara, Urtica dioica, Vaccinium myrtillus* and mixtures thereof, and an acceptable carrier.

In one particular embodiment, a composition includes the active ingredients of at least *Stachys betonica, Achillea millefolium, Marrubium vulgare,* and *Urtica dioica.* In other examples, a composition includes the active ingredients of at least *Stachys betonica, Achillea millefolium,* and *Marrubium vulgare.* In one example, a composition includes the active ingredients of at least *Stachys betonica, Achillea millefolium,* and *Urtica dioica.* In another example, the composition includes at least *Stachys betonica, Marrubium vulgare,* and *Urtica dioica.* In further examples, the composition includes at least *Achillea millefolium, Marrubium vulgare,* and *Urtica dioica.* In certain examples, the composition includes at least *Stachys betonica* and *Urtica dioica.* In some examples, the composition includes at least *Achillea mille-*

*folium* and *Marrubium vulgare*. In an example, the composition includes at least *Achillea millefolium* and *Urtica dioica*.

Also provided are pharmaceutical compositions including any of the disclosed compositions and an acceptable carrier/vehicle. In one example, the pharmaceutical composition is for use in the manufacture of a medicament or for use as a medicament.

In one particular example, a pharmaceutical composition for reducing or inhibiting bleeding comprises an about 1:1:1:1 mixture of *Achillea millefolium* (mother tincture 1×), *Urtica dioica* (mother tincture 1×), *Stachys betonica* (mother tincture 1×) and *Marrubium vulgare* (mother tincture 1×) combined within a gel base comprising about 0.02% (w/w) benzethonium chloride, about 2.5% (w/w) glycerin, about 2.5% (w/w) Tween 20, about 1.0% (w/w) aloe gel and about 92% (w/w) phosphate buffered saline and a thickener of about 2.4% (w/v) hydroxyethyl cellulose.

Any of the disclosed compositions can be provided by methods known to those of ordinary skill in the art, including topical administration, such as by a cream, ointment, gel, lotion, patch, spray, solution, suspension, emulsion, powder, enema, suppository, or a combination thereof.

Methods of use of the disclosed compositions are also provided, including methods of preventing or inhibiting a nosebleed, bleeding associated with a hemorrhoid or bleeding associated with an open-wound, such as a cut or abrasion. In one example, a method includes administering a therapeutically effective amount of at least one of the disclosed pharmaceutical compositions to a subject in need of reducing or inhibiting bleeding, thereby reducing or inhibiting the bleeding. In some examples, the method further includes selecting a subject in need of reducing or inhibiting bleeding, such as a subject who has a nosebleed, hemorrhoid or an open wound.

II. Terms

Unless otherwise noted, all technical terms and scientific terms used herein have the same meaning as commonly understood by one of skill in the art to which this disclosure belongs. As used herein, the singular forms "a," "an," and "the," refer to both the singular as well as plural, unless the context clearly indicates otherwise. For example, the term "a hemostatic active substance" includes single or multiple hemostatic active substances and can be considered equivalent to the phrase "at least one hemostatic active substance."

As used herein, the term "comprises" means "includes" without excluding other elements. The abbreviation, "e.g." is derived from the Latin exempli gratia, and is used herein to indicate a non-limiting example. Thus, the abbreviation "e.g." is synonymous with the term "for example." It is further to be understood that all concentrations given for the compositions are approximate, and are provided for description. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the disclosure, the following explanations of terms are provided:

Administer: To provide or give a subject a composition, such as a composition including a blood clotting agent by any effective route. Administration can be systemic or local. Exemplary routes of administration include, but are not limited to, topical e.g transdermal, buccal, vaginal, intranasal, rectal, inhalation, ocular, otic, enteral (e.g. oral, sublingual, buccal, rectal) and parenteral (e.g injections (such as subcutaneous, intramuscular, intradermal, intraperitoneal and intravenous) routes. In particular examples, compositions (such as those including a hemostatic active substance and an astringent active substance) are administered to a subject to prevent or stop bleeding.

Agent: Any protein, nucleic acid molecule, compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional agent induces the desired response (such as inducing a therapeutic or prophylactic effect when administered to a subject). In an example, an agent is a blood clotting agent. In a particular example, a blood clotting agent includes a hemostatic activity ingredient or substance. In other examples, a blood clotting agent includes an astringent active ingredient or substance. In some examples, a blood clotting agent includes at least one hemostatic activity substance and at least one astringent active substance.

Astringent active ingredient or substance: A substance or preparation that draws together or constricts body tissues and is effective in stopping the flow of blood or other secretions. Examples of astringent active ingredients, with astringent activity, include, but are not limited to *Acacia arabica, Agrimonia eupatoria, Azadirachta indica, Barosma, Bellis perennis, Bixa orellana, Carduus benedictus, Cimicifuga racemosa, Crataegus, Derris pinnata, Equisetum arvense, Euphrasia officinalis, Geranium maculatum, Geranium robertianum, Geum urbanum, Gnaphalium uliginosum, Hamamelis virginiana, Haronga madgascariensis, Hydrastis Canadensis, Hypericum perforatum, Iris versicolor, Juglans cinerea, Juniperus communis, Lamium album, Larix decidua, Lonicera caprifolium, Lycopus Virginicus, Marrubium vulgare, Oxalis acetosella, Paullinia sorbilis, Plantago major, Ranunculus ficaria, Rhamnus frangula, Rheum, Schinus molle, Solidago virgaurea, Stachys betonica, Tribulus terrestris, Tussilago farfara, Urtica dioica, Vaccinium myrtillus* and mixtures thereof.

Carriers: Carriers (vehicles) useful in this disclosure are conventional. *Remington's Pharmaceutical Sciences*, by E. W. Martin, Mack Publishing Co., Easton, Pa., 19th Edition (1995) and Homeopathic Pharmacopeia of the United States, describe compositions and formulations suitable for pharmaceutical delivery of one or more therapeutic agents, such as one or more compositions that include at least one hemostatic active substance and at least one astringent active substance.

In general, the nature of the carrier will depend on the particular mode of administration being employed. For instance, formulations can include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate, sodium lactate, potassium chloride, calcium chloride, and triethanolamine oleate. In some particular examples, formulation vehicles or carriers include glyceryl dioleate, glyceryl monooleate (Arlacel 186/Capmul GMO), lecithin, oleic acid, polyethylene glycol 400, propylene glycol, sorbitan monolaurate (Span 20), sorbitan monooleate (Span 80), sorbitan trioleate (Span 85), poloxamer 407, polysorbate 20, polysorbate 80, and cyclodextrins.

Hemorrhoid: A swelling and inflammation of veins in the rectum and anus. In some examples, a hemorrhoid becomes irritated and is associated with itching and bleeding.

Hemostasis: The cessation or reduction of blood loss from a damaged blood vessel.

Hemostatic active ingredient or substance: A substance causing the arrest of bleeding by the physiological properties of vasoconstriction and coagulation or by surgical means. Examples of hemostatic active substance include *Aconitum napellus, Agrimonia eupatoria, Aralia quinquefolia, Astragalus menziesii, Bellis perennis, Bixa orellana, Carduus benedictus, Equisetum arvense, Hamamelis Virginiana, Helleborus niger, hydrastis canadensis, millefolium, Salvia officinalis, Solidago virgaurea, Thlaspi bursa-pastoris, Urtica dioica, Vaccinium myrtillus, Viscum album, Zingiber officinale* and mixtures thereof. Additional hemostatic substances include aminocaproic acid, topical thrombin, microfibrillar collagen, aluminum chloride, aprotinin, and desmopressin.

Hemostatic composition: A composition capable of promoting hemostasis.

Inhibit: To decrease, limit or block the action or function of a molecule. In an example, bleeding is decreased, limited or blocked by application of one or more of the disclosed compositions. For example, a disclosed composition causes vasoconstriction of a blood vessel thereby inhibiting or reducing bleeding, such as by a decrease of at least 10%, at least 20%, at least 50%, at least 70%, or at least 90%.

LM potencies: Also called "Q" potencies are a delivery system in which "LM" represents the Roman numeral for "50,000." They are called LM potencies because the dilution factor is 1/50,000—instead of other customary methods of 1/100 dilution (called "c" potencies).

Mother tincture: A solution of a botanical substance and alcohol or water made according to standards set by the HPUS (Homeopathic Pharmacopeia of the United States).

Pharmaceutical composition: A chemical compound or composition capable of inducing a desired therapeutic or prophylactic effect when properly administered to a subject. A pharmaceutical composition can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject). In a particular example, a pharmaceutical composition comprises a therapeutically effective amount of at least one blood clotting agent such as a hemostatic active substance and an astringent active substance to prevent, reduce or inhibit bleeding.

Subject: Living multi-cellular vertebrate organisms, a category that includes human and non-human mammals (such as laboratory or veterinary subjects). In an example, a subject is a human. In an additional example, a subject is selected that is in need of preventing or inhibiting bleeding. For example, the subject is either at risk of developing bleeding or has bleeding in need of cessation.

Therapeutic effective amount: An amount of a composition (such as a composition that is a blood clotting agent) that alone, or together with one or more additional therapeutic compositions (such as additional hemostatic agents or agents with blood clotting activities) induces the desired response, such as prevention or cessation of bleeding. In one example, it is the amount of a disclosed composition including a blood clotting agent to form a hemostatic mass. In some examples, it is an amount of a composition including a hemostatic active substance and an astringent active substance needed to prevent or delay the development of bleeding, cause regression of bleeding of an existing wound, or treat one or more signs or symptoms associated with bleeding, such as chronic nose bleeds in a subject. Ideally, a therapeutically effective amount provides a therapeutic effect without causing a substantial cytotoxic effect in the subject. The preparations disclosed herein are administered in therapeutically effective amounts.

In an example, a desired response is to reduce or inhibit bleeding. Bleeding does not need to be completed stopped for a therapeutic effect to be observed. For example, a composition can decrease bleeding by a desired amount, for example by at least 5%, at least 10%, at least 15%, at least 20%, at least 25%, at least 30%, at least 50%, at least 75%, or even at least 90%, as compared to a response in the absence of the composition.

The effective amount of a composition that includes a hemostatic active agent and an astringent, that is administered to a human or veterinary subject will vary depending upon a number of factors associated with that subject, for example the overall health of the subject. An effective amount of an agent can be determined by varying the dosage of the product and measuring the resulting therapeutic response, such as suppression of inflammation or an allergic reaction. Effective amounts also can be determined through various in vitro and in vivo studies. The disclosed compositions can be administered in a single dose, or in several doses, as needed to obtain the desired response. However, the effective amount of can be dependent on the source applied, the subject being treated, the severity and type of the condition being treated, and the manner of administration.

Under conditions sufficient for: A phrase that is used to describe any environment that permits the desired activity. In one example, includes administering a therapeutically effective amount of a composition that includes a hemostatic active substance and an astringent active substance sufficient to allow the desired activity. In particular examples the desired activity is suppressing or inhibiting bleeding.

Unit dose: A physically discrete unit containing a predetermined quantity of an active material calculated to individually or collectively produce a desired effect, such as a therapeutic effect. A single unit dose or a plurality of unit doses can be used to provide the desired effect, such as treatment of a disorder, for example bleeding disorder, including chronic nose bleeds.

Wound: A type of physical trauma wherein the skin is torn, broken, cut or punctured.

III. Compositions

Disclosed herein are compositions, such as compositions for clotting blood, such as for stopping a nose bleed. In one example, a disclosed composition is a blood clotting agent that includes at least one hemostatic active substance and at least one astringent active substance. In some examples, a disclosed composition includes at least one hemostatic active substance. In other examples, a disclosed composition includes at least one astringent active substance.

i. Hemostatic Active Substances

Exemplary hemostatic active substances include *Aconitum napellus, Agrimonia eupatoria, Aralia quinquefolia, Astragalus menziesii, Bellis perennis, Bixa orellana, Carduus benedictus, Equisetum arvense, Hamamelis Virginiana, Helleborus niger, hydrastis canadensis, millefolium, Salvia officinalis, Solidago virgaurea, Thlaspi bursa-pastoris, Urtica dioica, Vaccinium myrtillus, Viscum album, Zingiber officinale*, and mixtures thereof. Additional hemostatic substances include aminocaproic acid, topical thrombin, microfibrillar collagen, aluminum chloride, aprotinin, and desmopressin. The types of hemostatic active substances selected to include within the composition may depend upon the particular use of the composition as well as the types of astringent active substances selected. For example, it is contemplated that the various hemostatic active substances have varying degrees of hemostatic activity. It is also contemplated that the activity of the hemostatic substances may depend upon the type of astringent active substance selected. Thus, one of ordinary skill in the art may select a particular hemostatic active substance or a combination of specific hemostatic active substances based upon the degree of overall activity of the composition desired.

ii. Astringent Active Substances

The disclosed astringent active substances with astringent activity include *Acacia arabica, Agrimonia eupatoria, Azadirachta indica, Barosma, Bellis perennis, Bixa orellana, Carduus benedictus, Cimicifuga racemosa, Crataegus, Derris pinnata, Equisetum arvense, Euphrasia officinalis, Geranium maculatum, Geranium robertianum, Geum urbanum, Gnaphalium uliginosum, Hamamelis virginiana, Haronga madgascariensis, Hydrastis Canadensis, Hypericum perforatum, Iris versicolor, juglans cinerea, juniperus communis, lamium album, Larix decidua, Lonicera caprifolium, Lycopus virginicus, Marrubium vulgare, Oxalis acetosella, Paullinia sorbilis, Plantago major, Ranunculus ficaria, Rhamnus frangula, Rheum, Schinus molle, Solidago virgaurea, Stachys betonica, Tribulus terrestris, Tussilago farfara, Urtica dioica, Vaccinium myrtillus* and mixtures thereof. The types of astringent active substances selected to include within the composition may depend upon the particular use of the composition as well as the types of astringent active substance selected. For example, it is contemplated that the various astringent active substances have varying degrees of astringent activity. It is also contemplated that the activity of the astringent substances may depend upon the type or types of hemostatic active substances selected. Thus, one of ordinary skill in the art may select a particular astringent active substance or a combination of specific astringent active substances based upon the degree of overall activity of the composition desired.

In one embodiment, a composition is a blood clotting agent in accordance with the Homeopathic Pharmacopoeia of the United States (Section 201 (g)(1)) which is hereby incorporated by reference in its entirety as available on Feb. 25, 2010. In one example, a blood clotting agent includes one or more hemostatic agents such as *Aconitum napellus, Agrimonia eupatoria, Aralia quinquefolia, Astragalus menziesii, Bellis perennis, Bixa orellana, Carduus benedictus, Equisetum arvense, Hamamelis virginiana, Helleborus niger, Hydrastis canadensis, Achillea millefolium, Salvia officinalis, Solidago virgaurea, Thlaspi bursa-pastoris, Urtica dioica, Vaccinium myrtillus, Viscum album, Zingiber officinale* and mixtures thereof and at least one astringent active ingredient, with astringent activity, such as *Acacia arabica, Agrimonia eupatoria, Azadirachta indica, Barosma, Bellis perennis, Bixa orellana, Carduus benedictus, Cimicifuga racemosa, Crataegus, Derris pinnata, Equisetum arvense, Euphrasia officinalis, Geranium maculatum, Geranium robertianum, Geum urbanum, Gnaphalium uliginosum, Hamamelis virginiana, Haronga madgascariensis, Hydrastis Canadensis, Hypericum perforatum, Iris versicolor, Juglans cinerea, Juniperus communis, Lamium album, Larix decidua, Lonicera caprifolium, Lycopus virginicus, Marrubium vulgare, Oxalis acetosella, Paullinia sorbilis, Plantago major, Ranunculus ficaria, Rhamnus frangula, Rheum, Schinus molle, Solidago virgaurea, Stachys betonica, Tribulus terrestris, Tussilago farfara, Urtica dioica, Vaccinium myrtillus* and mixtures thereof, and an acceptable carrier. For example, a blood clotting agent includes the active ingredients of at least *Stachys betonica, Achillea millefolium, Marrubium vulgare*, and *Urtica dioica*. In other examples, the blood clotting agent includes *Stachys betonica, Achillea millefolium*, and *Marrubium vulgare*. In one example, the blood clotting agent includes Stachys betonica, Achillea millefolium, and *Urtica dioica*. In another example, the blood clotting agent includes at least *Stachys betonica, Marrubium vulgare*, and *Urtica dioica*. In further examples, the blood clotting agent includes at least *Achillea millefolium, Marrubium vulgare*, and *Urtica dioica*. In certain examples, the blood clotting agent includes at least *Stachys betonica* and *Urtica dioica*. In some examples, the blood clotting agent includes at least *Achillea millefolium* and *Marrubium vulgare*. In an example, the blood clotting agent includes at least *Achillea millefolium* and *Urtica dioica*.

iii. Additional Hemostatic or Astringent Substances

Any of the disclosed compositions can further include one or more additional hemostatic and/or astringent substances. Additional exemplary hemostatic substances include, but are not limited to aminocaproic acid, topical thrombin, microfibrillar collagen, aluminum chloride, aprotinin, desmopressin, or any combination thereof. Additional examples of astringent substances include Alum, acetic acid with aluminum acetate (such as DOMEBORO®), witch hazel or any combination thereof.

IV. Pharmaceutical Compositions

Provided herein are pharmaceutical compositions including any of the disclosed compositions and an acceptable carrier. The pharmaceutical composition may also include one or more agents or drugs as known to be therapeutically active in the treatment of a bleeding disorder. The pharmaceutical composition may be administered topically, for example, using a multi-dose nasal spray bottle for delivery to the nasal passages. In one particular example, a disclosed pharmaceutical composition including active ingredients of *Stachys betonica, achillea millefolium, marrubium vulgare*, and *urtica dioica* is administered via a multi-dose nasal spray applicator. In some examples, the disclosed pharmaceutical compositions are administered, but not limited to, a cream, ointment, gel, lotion, patch, spray, solution, suspension, emulsion, powder, suppository, enema, liquid, syrup, elixir, and shampoo. In some examples, a disclosed clotting agent is administered via gauze, sponge, swab, multi-dose spray applicator, unit dose spray applicator. The pharmaceutical composition may also be administered orally. Additional routes of administration may include oral, sublingual, or transmucosal. In one example, the pharmaceutical composition is for use in the manufacture of a medicament or for use as a medicament.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical compositions for oral use can be formulated, for example, as tablets, troches, lozenges, aqueous or oily suspensions, dispersible powders or granules, emulsion hard or soft capsules, or syrups or elixirs. Such compositions can be prepared according to standard methods known to the art for the manufacture of pharmaceutical compositions and may contain one or more agents selected from the group of sweetening agents, flavoring agents, coloring agents and preserving agents in order to provide pharmaceutically elegant and palatable preparations. Tablets contain the active ingredient in admixture with suitable non-toxic pharmaceutically acceptable excipients including, for example, inert diluents, such as calcium carbonate, sodium carbonate, lactose, calcium phosphate or sodium phosphate; granulating and disintegrating agents, such as corn starch, or alginic acid; binding agents, such as starch, gelatin or acacia, and lubricating agents, such as magnesium stearate, stearic acid or talc. The tablets can be uncoated, or they may be coated by known techniques in order to delay disintegration and absorption in the gastrointestinal tract and thereby provide a sustained action over a longer period. For example, a time delay material such as glyceryl monostearate or glyceryl distearate may be employed. Pharmaceutical compositions for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium such as peanut oil, liquid paraffin or olive oil.

Pharmaceutical compositions can include pharmaceutically acceptable salts of the disclosed compositions. Pharmaceutically acceptable salts of the presently disclosed compounds include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. Pharmaceutically acceptable salts are also inclusive of the free acid, base, and zwitterionic forms. Description of suitable pharmaceutically acceptable salts can be found in Handbook of Pharmaceutical Salts, Properties, Selection and Use, Wiley VCH (2002).

Delivery systems and treatment regimens useful for such agents are known and can be used to administer these agents as therapeutics. The amount of the therapeutic agent that will be effective depends on the nature of the disorder or condition to be treated, as well as the stage of the disorder or condition. Effective amounts can be determined by standard techniques known to those of ordinary skill in the art. The precise dose to be employed in the formulation may vary depending upon the route of administration, and should be decided according to the judgment of the health care practitioner and each patient's circumstances. For example, the specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the host undergoing therapy.

The therapeutic agents of the present disclosure can be administered at about the same dose throughout a treatment period, in an escalating dose regimen, or in a loading-dose regime (for example, in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. In some examples, long-term treatment with a disclosed therapeutic is contemplated, for instance in order to prevent nose bleeds.

Single or multiple administrations of the composition comprising one or more of the disclosed compositions can be carried out depending upon the needs of the subject. For an acute bleeding, such as a nosebleed associated with a cut or abrasion (e.g., one experience during an isolated incidence, such as from a child falling on the playground) a single dose of the composition can be applied to the site of bleeding to reduce or inhibit bleeding. In a subject who experiences chronic bleeding, such as chronic nosebleeds, generally multiple doses are administered. In a particular example, the composition is administered once per day to the site of bleeding, such as to the nasal passage. However, the composition can be administered twice per day, three times per day, four times per day, six times per day, every other day, twice a week, weekly, monthly or as needed. Treatment for a chronic bleeding, such as chronic nosebleeds, will typically continue for at least a month, more often for two or three months, sometimes for six months or a year, and may even continue indefinitely, i.e., chronically. Repeat courses of treatment are also possible. In some examples, the compositions are provided to a subject in which the bleeding disorder is in remission, and the composition is provided as a preventive method of inhibiting reoccurrence of the bleeding disorder, such as chronic nosebleeds such as those caused by dry nasal passages. For example, a subject known to suffer from chronic nosebleeds that are currently in remission is selected and a therapeutic effective concentration of one or more of the disclosed compositions is administered to the subject, such as to the nasal passage. In some examples, this preventive or maintenance treatment program is provided daily, every other day, every three days or every week for at least a month, such as at least three months, six months or a year, or indefinitely.

In one embodiment, the pharmaceutical composition is administered without concurrent administration of a second agent for the treatment of a bleeding disorder. In one specific, non-limiting example, one or more of the disclosed compositions is administered without concurrent administration of other agents, such as without concurrent administration of an additional agent also known to reduce or inhibit bleeding. In other specific non-limiting examples, a therapeutically effective amount of a disclosed pharmaceutical composition is administered concurrently with an additional agent, including an additional agent known to inhibit or reduce bleeding. For example, the disclosed compounds are administered in combination with anti-oxidants, anti-inflammatory drugs or combinations thereof.

In one particular example, a pharmaceutical composition comprises one or more hemostatic active substances, one or more astringent active substances and a vehicle/carrier. Exemplary vehicles/carriers include, but are not limited to, glyceryl dioleate, glyceryl monooleate (Arlacel 186/Capmul GMO), lecithin, oleic acid, polyethylene glycol 400, propylene glycol, sorbitan monolaurate (Span 20), sorbitan monooleate (Span 80), sorbitan trioleate (Span 85), poloxamer 407, polysorbate 20, polysorbate 80, and cyclodextrins. In some examples, additional agents, such as buffering/pH adjustment agents, such as, but not limited to, sodium hydroxide/hydrochloric acid, acetic/citric acid, sodium acetate/citrate/phosphates, and potassium phosphates are included within the pharmaceutical composition. In further examples, additional agents such as osmolarity/tonicity adjusting agents (e.g., sodium chloride/potassium chloride, and glycine/glycerol), antioxidants/chelating agents/preservatives (e.g., EDTA, benzethonium chloride, benzyl alcohol, phenylethyl alcohol, and thimerosal) or viscosity modifiers (e.g., cellulose derivatives, povidone (PVP), and croscarmellose sodium) are included within a pharmaceutical composition. Other pharmaceutical vehicles/carriers, additional buffer/pH adjustment agents and antioxidants/chelating agents/preservations known to those of ordinary skill in the art are also considered to be within the scope of the present disclosure and can be administered concurrently or non-currently with the disclosed compositions.

In one example, concentrations of the hemostatic active substance or the astringent active substance range from 1×-1LM or higher. For example, the hemostatic active substance or the astringent active substance can be provided from a mother tincture with a 1× potency. As one of skill in the art will appreciate, different ratios and/or potencies of the various active substances can be utilized depending upon the use of the composition. For example, ratios may vary depending upon the site of action, tissue type and the like to accommodate different needs. For example, a composition including a higher amount of or a more active (stronger) astringent active substance as compared to the hemostatic active substance may be employed, if the bleeding is at a site where more action is first desired to constrict some of the smaller blood vessels and then a hemostatic agent is present (at a lower concentration/ratio) to complete the process of clotting.

It is contemplated that the ratio of one astringent active substance to one hemostatic active substance may vary from at least 0.1 to 10 (weight to weight), such as 1 to 1, 2 to 1, 3 to 1, 4 to 1, 5 to 1, 7.5 to 1, or 9 to 1 (weight to weight). In some embodiments, the ratio of one hemostatic active substance to one astringent active substance may vary from at least 0.1 to 10 (weight to weight), such as 1 to 1, 2 to 1, 3 to 1, 4 to 1, 5 to 1, 7.5 to 1, or 9 to 1 (weight to weight). In some embodiments, a composition includes two or more astringent active substances or two or more hemostatic active substances. In one example, the ratio of a first hemostatic active substance to a second hemostatic active substance may vary from at least 0.1 to 10 (weight to weight), such as 1 to 1, 2 to 1, 3 to 1, 4 to 1, 5 to 1, 7.5 to 1, or 9 to 1 (weight to weight). In other examples, the ratio of a first astringent active substance to a second astringent active substance may vary from at least 0.1 to 10 (weight to weight), such as 1 to 1, 2 to 1, 3 to 1, 4 to 1, 5 to 1, 7.5 to 1, or 9 to 1 (weight to weight).

It is contemplated that the concentrations of additional agents included within the pharmaceutical compositions such as vehicles/carriers, additional buffer/pH adjustment agents and antioxidants/chelating agents/preservations may vary depending upon various factors, including the use of the composition. For example, a gel base can be used that includes about 0.01% (w/w) to about 1% (w/w) benzethonium chloride, about 1% (w/w) to about 10% (w/w) glycerin, about 1% (w/w) to about 10% (w/w) Tween 20, about 0.1% to about 5% (w/w) aloe gel, about 80% to about 98% (w/w) phosphate buffered saline, or a combination thereof. In some examples, the pharmaceutical composition also includes a thickener, such as about 1% to about 10% (w/v) hydroxyethyl cellulose.

In one particular example, a pharmaceutical composition for reducing or inhibiting bleeding, an about 1:1:1:1 mixture of *Achillea millefolium* (mother tincture 1×), *Urtica dioica* (mother tincture 1×), *Stachys betonica* (mother tincture 1×) and *Marrubium vulgare* (mother tincture 1×). For example, such active substances can be combined within a gel base, such as a gel base comprising about 0.02% (w/w) benzethonium chloride, about 2.5% (w/w) glycerin, about 2.5% (w/w) Tween 20, about 1.0% (w/w) aloe gel and about 92% (w/w) phosphate buffered saline and a thickener, such as of about 2.4% (w/v) hydroxyethyl cellulose.

V. Methods of Use

It is shown herein that a composition including *Stachys betonica, Achillea millefolium, Marrubium vulgare*, and *Urtica dioica* can be used to stop a nosebleed. Based on this observation, new methods of preventing, reducing or inhibiting bleeding are disclosed, for example by using compositions including *Stachys betonica, Achillea millefolium, Marrubium vulgare*, and *Urtica dioica* to inhibit or prevent a nosebleed, bleeding associated with other disorders including hemorrhoids (external and/or internal hemorrhoids) and/or a cut or abrasion.

Methods of preventing or inhibiting bleeding are disclosed. In one example, a method includes administering a therapeutically effective amount of at least one of the disclosed pharmaceutical compositions to a subject in need of reducing or inhibiting bleeding, thereby reducing or inhibiting the bleeding. In one example, the method further includes selecting a subject in need of reducing or inhibiting bleeding, such as a subject who has a nosebleed, hemorrhoid or an open wound. For example, selecting the subject in need of reducing or inhibiting bleeding comprises selecting a subject having a bleeding disorder. In one example, the bleeding disorder is chronic nosebleeds. In some examples, selecting the subject in need of reducing or inhibiting bleeding comprises selecting a subject having bleeding associated with hemorrhoids. In other examples, selecting the subject in need of reducing or inhibiting bleeding comprises selecting a subject having an open wound, a cut or abrasion. In some examples, subjects are initially screened to determine if they are in need of reducing or inhibiting bleeding, whether they have a condition or disease associated with undesirable bleeding or combinations thereof. For example, the clinical symptoms known to those of skill in the art to be associated with a bleeding disorder can be used to screen subjects to determine if they are candidates for the disclosed therapies.

The method can reduce or inhibit bleeding and thus cause blood to clot either in vitro or in vivo. When reducing bleeding in vivo, the composition can be used to either avoid bleeding or to treat an existing condition. The bleeding may be associated with a primary bleeding disorder (such as chronic nosebleeds also known as epistaxis), meaning that it is not secondary to another disorder that causes bleeding as a consequence of the primary disorder. The disclosed methods can be used to reduce or inhibit bleeding associated with a disorder or a disease, such as, but not limited to, chronic nosebleeds or hemorrhoids. Reduction or inhibition of bleeding can include a partial reduction in bleeding such as by at least 10% (such as by at least 20%, at least 50%, or at least 90%) as compared to a response in the absence of one or more disclosed compositions. For example, bleeding associated with a nosebleed can be suppressed by at least 10% (such as by at least 20%, at least 50%, or at least 90%) as compared to bleeding in the absence of the treatment.

Therapeutically Effective Concentrations

The methods can include administering a composition including a therapeutically effective amount of at least one hemostatic active substance and a least one astringent active substances as described in detail above. Additional agents can also be administered to the subject, such as additional hemostatic or astringent agents as well as additional coagulants in combination with the disclosed compositions. Therapeutically effective amounts induce the desired response (e.g., prevention, reduction or inhibition of bleeding, such as that associated with a nosebleed, hemorrhoids, or a cut/abrasion.

Screening Subjects

Subjects can be screened prior to initiating the disclosed therapies, for example to select a subject in need of preventing, reducing or inhibiting bleeding, such as a subject having or at risk of developing bleeding, such as a nosebleed or bleeding associated with hemorrhoids, surgery, a cut or abrasion. Briefly, the method can include screening subjects to determine if they are in need of preventing, reducing or inhibiting bleeding. Subjects having bleeding or at risk of developing bleeding are selected. In one example, subjects are diagnosed with the bleeding condition by clinical signs, laboratory tests, or both. For example, subjects can be diagnosed by characteristic clinical signs, such as chronic nosebleeds or a dry nasal passage. Diagnosis is generally by visual observation. For example, a subject experiencing one or more nosebleeds a week indicates that the bleeding can be treated using the compositions and methods provided herein, such as by daily application of one or more of the disclosed compositions to the nasal passage as a preventive method of controlling nose bleeding.

Pre-screening is not required prior to administration of the therapeutic agents disclosed herein. Dosages, routes of administration of the disclosed pharmaceutical compositions for the methods of treatment as well as possible administration of additional therapeutic agents are known to those of skill in the art, but are not limited to those described previously herein and the Examples.

Exemplary Conditions or Disorders

The disclosed compositions and methods can also be used to prevent, reduce or inhibit nosebleeds that often occur in subjects while they are engaged in physical activities, including, but not limited to, general child or adult physical activities, in particular, contact sports or other sports where contact may occur with the nose (e.g., wrestling, boxing, mixed martial arts, basketball, soccer, rugby, baseball, volleyball, football and like activities). The disclosed compositions and methods can also be used to prevent nasal passages from becoming dry and resulting in a nosebleed, such as can occur during exposure dry air (e.g., including conditions that occur during air travel, in dry climates, or during outdoor winter sport activities where nasal membranes become dry). In some examples, the disclosed compositions and methods are used in conjunction with or in lieu of traditional therapies used to prevent or treat bleeding disorders (such as hemophilia or hereditary hemorrhagic telangiectasia). In one example, the disclosed compositions and methods are provided to prevent or inhibit a nosebleed in a subject who is currently taking a blood thinner agent or is pregnant. Methods of use for preventing, reducing or inhibiting a nosebleed associated with any of the aforementioned conditions include contacting an inner nasal passageway with a disclosed composition under conditions sufficient to prevent, reduce or inhibit the nosebleed (as described in detail herein).

The disclosed compositions and methods can also be used to reduce or inhibit bleeding associated with cuts, abrasions or bruises, such as those acquired during physical activity, such as contact sports and other sports where contact may occur with any part of the body or during surgery. In one example, the disclosed compositions and methods are used to prevent further bleeding from cuts or wounds caused by such physical activities (for example, cuts acquired during a boxing match, martial arts or other contact sports). In one particular example, one or more of the disclosed compositions or methods is used to reduce or inhibit bleeding caused by activity associated with a cosmetologist, hairstylist, barber, chef, carpenter or any profession that works with sharp utensils that may cause bleeding. For example, any one of the disclosed compositions can be provided within a kit, such as a first aid kit with other products that are used in case of emergency. It is contemplated that the disclosed compositions can be used on both human subjects and veterinary animals, such as during nail trimming, surgical operations or other activities in which undesired bleeding may occur.

Assessment

Following the administration of one or more therapies, subjects having bleeding (for example, bleeding associated with a nosebleed) can be monitored for decreases or cessation in bleeding or in one or more clinical symptoms associated with the bleeding (including preventing further bleeding and/or symptoms associated with bleeding, including dry nasal passage). In particular examples, subjects are analyzed one or more times, starting one minute following treatment. Subjects can be monitored using any method known in the art including those described herein, including visual observation.

Additional Treatments

In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 10%, at least 20%, at least 30%, at least 40%, at least 50%, at least 70%, at least 90% or more in bleeding. It is also contemplated that a subject can continue to use one or more of the disclosed compositions as a method to prevent bleeding, such as a nosebleed, in the future.

The following examples are provided to illustrate certain particular features and/or embodiments. These examples should not be construed to limit the invention to the particular features or embodiments described.

EXAMPLES

Example 1

This example illustrates the ability of a disclosed composition to effectively inhibit bleeding. Nose bleeding was caused by creating an abrasion to the nasal passage of a subject by use of a cotton swab irritating the nasal passage. The subject then blew their nose vigorously. The first test was to create an abrasion and pinching the nostril with no application of any product. Bleeding was checked at multiple time points, including the after 30 seconds, 60 seconds and 90 seconds by blowing ones nose 3 times and dabbing the area with a tissue to see if there was continued perfuse bleeding. At each time point, bleeding continued in the nasal passage. After 90 seconds, the first test was then concluded.

Next, the effect of glycerin on nose bleeding was determined. Glycerin was applied to the nasal passage after bleeding had started. Bleeding was checked at multiple time points, including the after 30 seconds, 60 seconds and 90 seconds by blowing ones nose 3 times and dabbing the area with a tissue to see if there was continued perfuse bleeding. At each time point, bleeding continued in the nasal passage. After 90 seconds, the second test was then concluded.

The effect of the disclosed clotting agent that included the active ingredients of *Stachys betonica, achillea millefolium, marrubium vulgare*, and *urtica dioica* application on nose bleeding was then determined. Bleeding was checked at multiple time points, including after 30 seconds, 60 seconds and 90 seconds by the subject blowing their nose 3 times and dabbing the area with a tissue to see if there was continued perfuse bleeding. After 30 seconds, there was still bleeding. After 1 minute, there was still bleeding, but by visual inspection the quantity of blood was less. After 90 seconds, there was no bleeding in the nasal passage. This part of the test was then concluded.

These studies demonstrate that the disclosed clotting agent has hemostatic activities and may be useful to treat nose bleeds Example 2

Nasal Formulation General Preparation Technique

This example provides a preparation technique for a nasal formulation for one of the disclosed compositions. The following extracts were used to prepare the nasal formulation: Betony, Teeter Creek lot #8419000193; Horehound, Teeter Creek lot #8419000103; *Urtica Dioica* (Nettles), Teeter Creek lot #8419000183; and Yarrow, Teeter Creek lot #8419000339. Equal volumes of each extract were added to a glass vial. During preliminary formulation development, 0.5 mL of each extract was used for a total of 2.0 mLs. The extract mixture was dried under nitrogen. Formulation vehicle was prepared using the ingredients listed in Table 1. An aliquot of formulation vehicle equal in volume to the total volume of the starting tincture mixture in step 1 (e.g., 2.0 mLs) was added to the vials dried in step 2. The vials were vortexed and sonicated to thoroughly reconstitute the dried tinctures.

TABLE 1

Vehicle Preparation (Percentage is based on the weight of the final product)

|  | Preparation #1 | Preparation #2 |
|---|---|---|
| Benzethonium Chloride | 0.02% (w/w) | 0.02% (w/w) |
| Glycerin | 2.5% (w/w) | 2.5% (w/w) |
| Polysorbate 20 | 2.5% (w/w) | 2.5% (w/w) |
| Carboxymethyl Cellulose | 0.15% | 2.0% (w/w) |
| Phosphate Buffered Saline | 94.83% (w/w) | 92.98% (w/w) |

Starting vehicle component percentages were based on levels reported in the FDA's Inactive Ingredient List for nasal formulations. Preparation #1 containing only 0.15% (w/w) carboxymethyl cellulose was not viscous enough to stay in the nasal cavity. Preparation #2 which contained 2.5% (w/w) carboxymethyl cellulose and 2.5% (w/w) hydroxyethyl cellulose, had improved viscosity. However, the dried extract mixture was difficult to reconstitute when the thickener was added to the vehicle. Aggressive mixing techniques such as homogenization caused excessive foaming with several visible particles.

To improve the overall formulation, a two-step mixing procedure was used for reconstituting the dried tinctures with the formulation vehicle components and alternative mother tinctures were obtained for the next development batches. These results are provided in Example 3.

Example 3

Nasal Formulation General Preparation Technique

This example provides a preparation technique for a nasal formulation of a composition for preventing, reducing or inhibiting bleeding. It is contemplated that a similar preparation technique can be used to prepare formulations suitable to treat hemorrhoids, cuts or bruises, or an open-wound, such as that associated with surgery.

The following four tinctures were utilized: *Urtica Dioica* (Nettles), Standard Homeopathic lot # RP14968; *Millefolium* (Yarrow), Standard Homeopathic lot # RP68048; *Marrubium Vulg.* (Horehound), Standard Homeopathic lot # RP43234; and *Stachys Betonica* (Betony), Standard Homeopathic lot #30932. Equal volumes of each tincture were added to a glass vial. During formulation development, 1.0 mL of each tincture was used for a total of 4.0 mLs. The tincture mixture was dried under nitrogen. Formulation vehicle was prepared using the ingredients listed in Table 2. An aliquot of formulation vehicle equal in volume to the total volume of the tincture mixture in step 1 (e.g., 4.0 mLs) was added to the vials dried in step 2. The vials were vortexed and sonicated to thoroughly reconstitute the dried tinctures. A small aliquot of this solution was removed for assay. A cellulose based thickener was weighed into each vial. The quantities are included in Table 3. The solutions were stirred on a magnetic stir plate overnight to thoroughly mix. The resulting mixture was clear amber color with no visible particles or foaming. This preparation providing a formulation that can be used to prevent, reduce or inhibit bleeding in accordance with the teachings herein.

TABLE 2

Vehicle Preparation (Percentage is based on the weight of the final product)

|  | Preparation #1 | Preparation #2 | Preparation #3 |
|---|---|---|---|
| Benzethonium Chloride | 0.02% (w/w) | 0.02% (w/w) | 0.02% (w/w) |
| Glycerin | 2.5% (w/w) | 2.5% (w/w) | 2.5% (w/w) |
| Polysorbate 20 | 2.5% (w/w) | 2.5% (w/w) | 2.5% (w/w) |
| Aloe Gel |  | 1.0% (w/w) | 1.0% (w/w) |
| Phosphate Buffered Saline | 90.98% (w/w) | 89.98% (w/w) | 91.58% (w/w) |

TABLE 3

Thickener Amounts (Percentage is based on the weight of the final product)

|  | Preparation #1 | Preparation #2 | Preparation #3 |
|---|---|---|---|
| Carboxymethyl Cellulose | 2.0% (w/w) |  |  |
| Hydroxyethyl Cellulose | 2.0% (w/w) | 4.0% (w/w) | 2.4% (w/w) |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. A composition for reducing bleeding, consisting of *Achillea Millefoliurn, Urtica dioica* and a vehicle mixture with a cellulose based thickener, wherein the *Achillea millefolium* is *Achillea millefolium* (mother tincture 1×) and *Urtica dioica* is *Urtica dioica* (mother tincture 1×) and the vehicle mixture with a cellulose based thickener is 2.5% (w/w) hydroxyethyl cellulose and 2.5% (w/w) carboxymethyl cellulose or 2.0% (w/w) hydroxyethyl cellulose and 2.0% (w/w) carboxymethyl cellulose.

2. A composition for reducing bleeding consisting of *Achillea millefolium* (mother tincture 1×), *Urtica dioica* (mother tincture 1×) an effective amount of a vehicle carrier, an effective amount of a pH adjustment agent, an effective amount of a osmolarity/tonicity adjusting agent and an effective amount of a viscosity modifier, wherein *Achillea Millefohum*(mother tincture 1×) is present at an effective amount for hemostatic activity, *Urtica dioica* (mother tincture 1×) is present at an effective amount for hemostatic activity and vehicle carrier, pH adjustment agent, osmolarity/tonicity adjusting agent and a cellulose based viscosity modifier are present at effective amounts to form an effective gel-based composition capable of adhering to a bleeding site for reducing bleeding.

3. The composition of claim 2, wherein the vehicle carrier is aloe gel, glycerin, polysorbate 20, phosphate buffered saline, benzethonium chloride, water or a combination thereof.

4. The composition of claim 2, wherein the pH adjustment agent is citric acid, sodium acetate/citrate/phosphates, potassium phosphates or a combination thereof.

5. The composition of claim 2, wherein the osmolarity/tonicity adjusting agent is sodium chloride, potassium chloride, glycine, glycerol or a combination thereof.

6. The composition of claim 2, wherein the cellulose based viscosity modifier is about 2% (w/w) cellulose hydroxyethyl and about 2% (w/w) cellulose carboxymethyl at an effective amount for use in a nasal cavity to reduce or inhibit bleeding.

7. A composition, for reducing bleeding, consisting of *Achillea Millefoliurn, Urtica dioica* and a vehicle mixture with a cellulose based thickener of equal proportions of hydroxyethyl cellulose and carboxymethyl cellulose sufficient for use in a nasal cavity to reduce bleeding.

8. The composition of claim 2, wherein the cellulose base viscosity modifier is carboxymethyl cellulose and hydroxyethyl cellulose.

9. The composition of claim 2, wherein the cellulose base viscosity modifier is hydroxyethyl cellulose.

\* \* \* \* \*